US00PP16500P2

(12) United States Plant Patent
Uchneat

(10) Patent No.: US PP16,500 P2
(45) Date of Patent: May 2, 2006

(54) **DOUBLE *IMPATIENS* PLANT NAMED 'BALOLEPURP'**

(50) Latin Name: *Impatiens walleriana*
Varietal Denomination: Balolepurp

(75) Inventor: Michael S. Uchneat, Geneva, IL (US)

(73) Assignee: Ball Horticultural Company, West Chicago, IL (US)

( * ) Notice: Subject to any disclaimer, the term of this patent is extended or adjusted under 35 U.S.C. 154(b) by 54 days.

(21) Appl. No.: 11/011,315

(22) Filed: Dec. 13, 2004

(51) Int. Cl.
*A01H 5/00* (2006.01)

(52) U.S. Cl. ..... Plt./317

(58) Field of Classification Search ..... Plt./317
See application file for complete search history.

*Primary Examiner*—Anne Marie Grunberg
*Assistant Examiner*—Annette H Para
(74) *Attorney, Agent, or Firm*—Wood, Phillips, Katz, Clark & Mortimer

(57) ABSTRACT

A new and district Double *Impatiens* plant named 'Balolepurp' characterized by its fully double dark purple-colored flowers, medium green-colored foliage, compact, upright and mounded growth habit, and good basal branching character.

1 Drawing Sheet

Latin Name of genus and species of plant claimed: *Impatiens walleriana.*
Variety denomination: 'Balolelpurp'.

BACKGROUND OF THE INVENTION

The present invention relates to a new and distinct cultivar of Double *Impatiens* plant botanically known as *Impatiens walleriana* and hereinafter referred to by the cultivar name 'Balolepurp'.

The new cultivar originated in a controlled breeding program during April 2000 at Elburn, Ill. The objective of the breeding program was the development of new *Impatiens* cultivars with numerous, fully double flowers, excellent basal branching, and upright compact growth habit.

The female (seed) parent of the new cultivar was the proprietary *Impatiens walleriana* selection designated 3177-1-1-2, not patented, characterized by its small, single, salmon-colored flowers. The male (pollen) parent of the new cultivar was the proprietary *Impatiens walleriana* selection designated 12865-2, not patented, characterized by its dark green-colored foliage. The new cultivar was discovered and selected by the inventor as a single flowering plant within the progeny of the stated cross-pollination during September 2001 at Elburn, Ill. Asexual reproduction of the new cultivar by terminal stem cuttings since September 2001 at West Chicago, Ill., has demonstrated that the new cultivar reproduces true to type with all characteristics, as herein described, firmly fixed and retained through successive generations of such asexual propagation.

SUMMARY OF THE INVENTION

The following characteristics of the new cultivar have been repeatedly observed and can be used to distinguish 'Balolepurp' as a new and distinct cultivar of Double *Impatiens* plant:

1. Fully double purple-colored flowers.
2. Medium green-colored foliage.
3. A good basal branching character.
4. A compact, upright and mounded growth habit.

Plants of the new cultivar differ from plants of the female parent primarily in flower form and color and from the male parent primarily in foliage color.

Of the many commercially available Double *Impatiens* cultivars known to the inventor, the most similar to the new cultivar is the *Impatiens walleriana* variety 'Balfiepuna', U.S. Plant Pat. No. 13,611. However, in side-by-side comparisons conducted at West Chicago, Ill., plants of the new cultivar differed from plants of 'Balfiepuna' in the following characteristics:

1. Plants of the new cultivar are shorter than plants of 'Balfiepuna'.
2. The leaves of the new cultivar are smaller than the leaves of 'Balfiepuna'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describe the colors of 'Balolepurp'. The plants were grown for 8 weeks in a greenhouse at West Chicago, Ill.

DETAILED BOTANICAL DESCRIPTION

Figure 1:
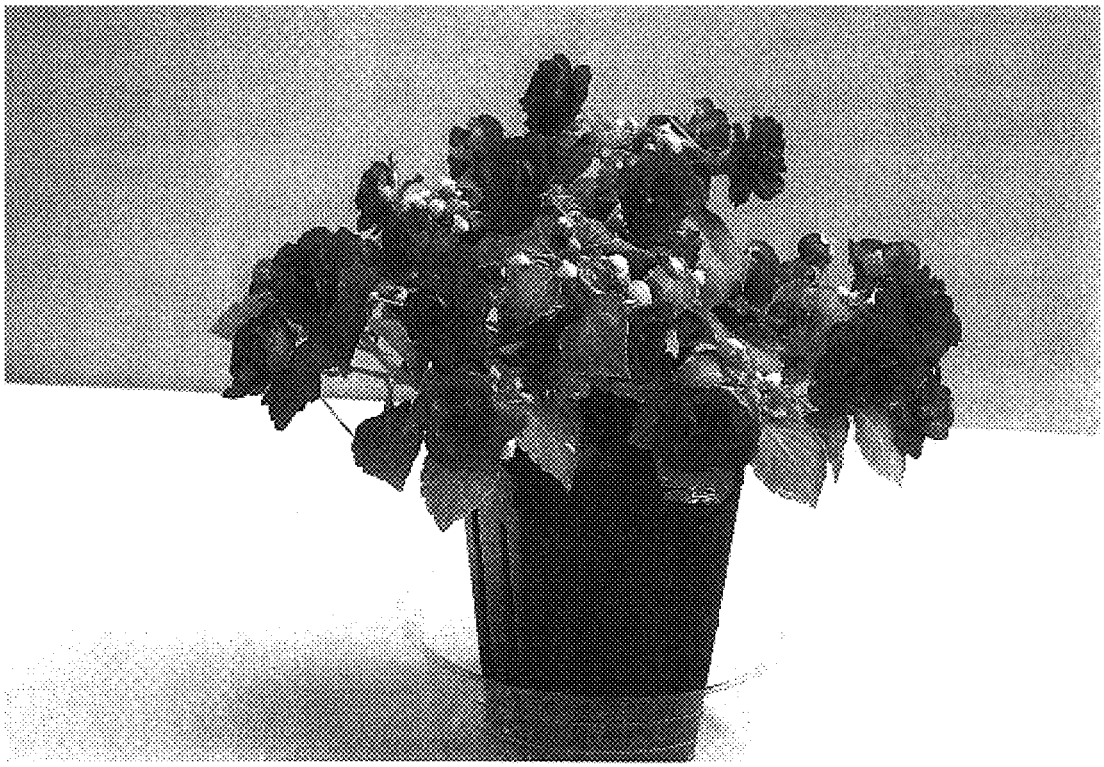
FIG. 1 illustrates a side view of the overall growth and flowering habit of 'Balolepurp'.
Figure 2:
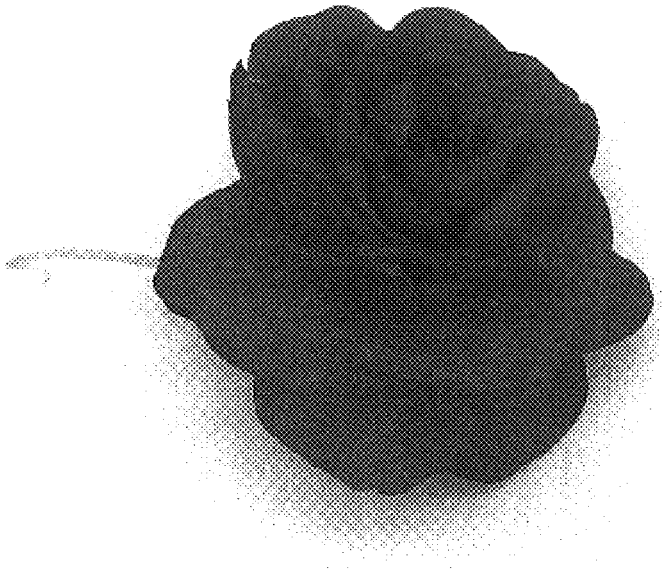
FIG. 2 illustrates a close-up view of an individual flower of 'Balolepurp'.

The new cultivar has not been observed under all possible environmental conditions to date. Accordingly, it is possible that the phenotype may vary somewhat with variations in the environment, such as temperature, light intensity, and day length without, however, any variance in phenotype.

The chart used in the identification of colors described herein is the R.H.S. Colour Chart of The Royal Horticultural Society, London, England, 2001 edition, except where general color terms of ordinary significance are used. The color values were determined on Jul. 20, 2004 between 10:00 and 11:45 a.m. under natural light conditions.

The following descriptions and measurements describe plants produced from cuttings taken from stock plants and grown in a double polycarbonate-covered greenhouse under conditions comparable to those used in commercial practice. The plants were grown at West Chicago, Ill. in 10 cm pots for 8 weeks using a soilless growth medium. Greenhouse temperatures were maintained at approximately 65°–75° F. during the day and approximately 55°–62° F. during the night. Greenhouse light levels were maintained at approximately 4,000–6,000 footcandles during the day.

Botanical classification: *Impatiens walleriana* cultivar Balolepurp.

Parentage:

*Female (seed) parent.*—Proprietary *Impatiens walleriana* selection designated 3177-1-1-2, not patented.

*Male (pollen) parent.*—Proprietary *Impatiens walleriana* selection designated 12865-2, not patented.

Propagation:

*Type cutting.*—Terminal stem.

*Time to initiate roots.*—Approximately 7–14 days.

*Time to produce a rooted cutting.*—Approximately 21 days.

*Root description.*—Fine, fibrous.

*Rooting habit.*—Freely branching.

Plant description:

*Crop time.*—Approximately 6–8 weeks from planting of rooted cutting to finish.

*Growth habit.*—Compact with good basal branching.

*Form.*—Upright and mounded.

*Size.*—Height: Approximately 12.9 cm. Width (area of plant spread): Approximately 24.9 cm in width (plant spread).

*Branch.*—Quantity: Approximately 3 per plant. Strength: Strong. Length: Approximately 12 cm. Diameter: Approximately 6.8 mm. Texture: Glabrous. Color: 144A. Internode length: Approximately 1.3 cm.

*Foliage.*—Quantity of leaves per branch: Approximately 11. Fragrance: None. Type: Simple. Arrangement: Alternate. Aspect: At right angle to stem. Shape: Ovate. Apex: Cuspidate. Base: Attenuate. Margin: Crenate/ciliate. Venation pattern: Pinnate, arcuate. Size of mature foliage: Length: Approximately 1.1 cm. Width: Approximately 8.9 mm. Texture of both surfaces: Glabrous. Color of upper surface of mature foliage: Darker than 137A, with veins and mid-vein of 144A. Color of lower surface of mature foliage: Closest to 138B with veins and mid-vein of 144C. Petiole length: Approximately 5.5 mm. Petiole diameter: Approximately 0.6 mm. Petiole texture: Both surfaces are glabrous. Petiole color: 144C.

Flowering description:

*Flowering habit.*—Freely flowering under outdoor growing conditions with substantially continuous blooming from spring through autumn and year round in greenhouse environment.

*Lastingness of individual bloom.*—Approximately 7–10 days.

*Quantity of flowers.*—Approximately 28 flowers and 20 buds per plant at any one time.

Flower description:

*Flower bud rate of opening.*—Generally it takes from 3–6 days for buds to progress from first color to fully open flowers.

*Mature flower buds (just before opening).*—Shape: Elliptic. Length: Approximately 1.1 cm. Diameter: Approximately 1 cm. Color: N74D.

*Flower description.*—Type: Fully double. Fragrance: None. Shape: Spherical. Diameter: Approximately 3.2 cm. Depth: Approximately 1.3 cm. Borne: Above foliage facing upward or outward. Flowers are not persistent or fragrant.

*Petals.*—Quantity per flower: Approximately 29. Shape: Obovate. Margin: Entire. Apex: Retuse. Base: Attenuate. Texture: Glabrous. Appearance: Iridescent. Size of outermost petals: Length: Approximately 1.8 cm. Width: 1.6 cm. Size of innermost petals: Length: 1.2 cm. Width: 1 cm.

*Flower color.*—Upper surface of petals when fully open: Slightly darker than N74A. Lower surface of petals when fully open: Closest to N74D. Petal color fading with age to: 83A.

*Calyx.*—Quantity of sepals: Three, with the lower sepal modified into a spur. Sepal apex: Acuminate. Sepal texture: Both surfaces are glabrous. Lateral sepal shape: Lanceolate. Lateral sepal apex: Acute. Lateral sepal length: Approximately 3 mm. Lateral sepal width: Approximately 1 mm. Lateral sepal color: Both surfaces are 144C. Lower sepal shape: Ovate. Lower sepal apex: Acute. Lower sepal base forms spur. Lower sepal length: Approximately 7 mm. Lower sepal width: Approximately 7 mm. Lower sepal, color of both surfaces: 154D with N144D at tip.

*Spur.*—Quantity: One per flower. Length: Approximately 1.1 cm. Diameter at base: Approximately 2 mm. Diameter at tip: Approximately 1 mm. Texture: Glabrous. Color: 154D with overlay of 71B.

*Peduncles.*—Length: Approximately 2 cm. Diameter: Approximately 0.4 mm. Texture: Glabrous. Strength: Strong. Angle to stem: Acute. Color: 144C.

*Reproductive organs.*—None observed.

Seed and fruit development: Neither seed nor fruit production has been observed.

Disease and pest resistance: Resistance to pathogens and pests common to *Impatiens* has not been observed.

What is claimed is:

1. A new and distinct cultivar of Double *Impatiens* plant named 'Balolepurp', substantially as herein shown and described.

* * * * *